United States Patent
Dhillon et al.

(10) Patent No.: US 10,288,478 B2
(45) Date of Patent: May 14, 2019

(54) PHOTOCONDUCTIVE ANTENNA FOR TERAHERTZ WAVES, METHOD FOR PRODUCING SUCH PHOTOCONDUCTIVE ANTENNA AND TERAHERTZ TIME DOMAIN SPECTROSCOPY SYSTEM

(71) Applicants: CENTRE NATIONAL DE LA RECHERCHE SCIENTIFIQUE, Paris (FR); ECOLE NORMALE SUPERIEURE, Paris (FR)

(72) Inventors: Sukhdeep Dhillon, Bourg la Reine (FR); Kenneth Maussang, Le Kremlin-Bicetre (FR)

(73) Assignees: CENTRE NATIONAL DE LA RECHERCHE SCIENTIFIQUE, Paris (FR); ECOLE NORMALE SUPERIEURE, Paris (FR)

( * ) Notice: Subject to any disclaimer, the term of this patent is extended or adjusted under 35 U.S.C. 154(b) by 24 days.

(21) Appl. No.: 15/534,774

(22) PCT Filed: Dec. 14, 2015

(86) PCT No.: PCT/IB2015/059592
§ 371 (c)(1),
(2) Date: Jun. 9, 2017

(87) PCT Pub. No.: WO2016/097975
PCT Pub. Date: Jun. 23, 2016

(65) Prior Publication Data
US 2017/0322078 A1    Nov. 9, 2017

(30) Foreign Application Priority Data
Dec. 17, 2014    (EP) ..................................... 14307065

(51) Int. Cl.
*G01J 3/02* (2006.01)
*G01J 3/28* (2006.01)
(Continued)

(52) U.S. Cl.
CPC ............... *G01J 3/0205* (2013.01); *G01J 3/28* (2013.01); *G01N 21/3586* (2013.01);
(Continued)

(58) Field of Classification Search
CPC ...... G01J 3/0205; G01J 3/28; G01N 21/3586; H01L 31/0304; H01L 31/08; H01L 31/09
See application file for complete search history.

(56) References Cited

U.S. PATENT DOCUMENTS

2012/0092223 A1* 4/2012 Habib ..................... H01Q 1/38
343/753

FOREIGN PATENT DOCUMENTS

JP    2011228572 A    11/2011

OTHER PUBLICATIONS

Madeâo J et al., "Frequency tunable terahertz interdigitated photoconductive antennas", Electronic Letters, pp. 611-613, vol. 46, No. 9 (Apr. 2010).

* cited by examiner

Primary Examiner — Mark R Gaworecki
(74) Attorney, Agent, or Firm — Browdy and Neimark, P.L.L.C.

(57) ABSTRACT

The present invention relates to a metal-metal interdigitated photoconductive antenna that generates and/or detects terahertz waves, the photoconductive antenna comprising at least one substrate (1) and at least one electrode (2) on the front face of the substrate (1), wherein said photoconductive antenna comprises at least one layer (4) formed of a material reflective to terahertz waves, said layer (4) extending below (Continued)

the front face of the substrate (1) at a distance lower than the wavelength; and it comprises an interdigitated geometry on said front face of the substrate (1) comprising a first metallization layer of 5 nm Cr and 150 nm Au for the interdigitated electrodes (2), equally spaced by a distance Δ, is made on said front face of the substrate (1); a 500 nm-thick layer of $SiO_2$ (5) deposited over the first metallization layer; and a second metallic layer composed of metallic fingers (6) covering gaps with a periodicity double that of the distance Δ.

16 Claims, 6 Drawing Sheets

(51) Int. Cl.
  *G01N 21/35* (2014.01)
  *H01L 31/08* (2006.01)
  *H01L 31/09* (2006.01)
  *G01N 21/3586* (2014.01)
  *H01L 31/0304* (2006.01)
(52) U.S. Cl.
  CPC .............. *H01L 31/08* (2013.01); *H01L 31/09* (2013.01); *H01L 31/0304* (2013.01)

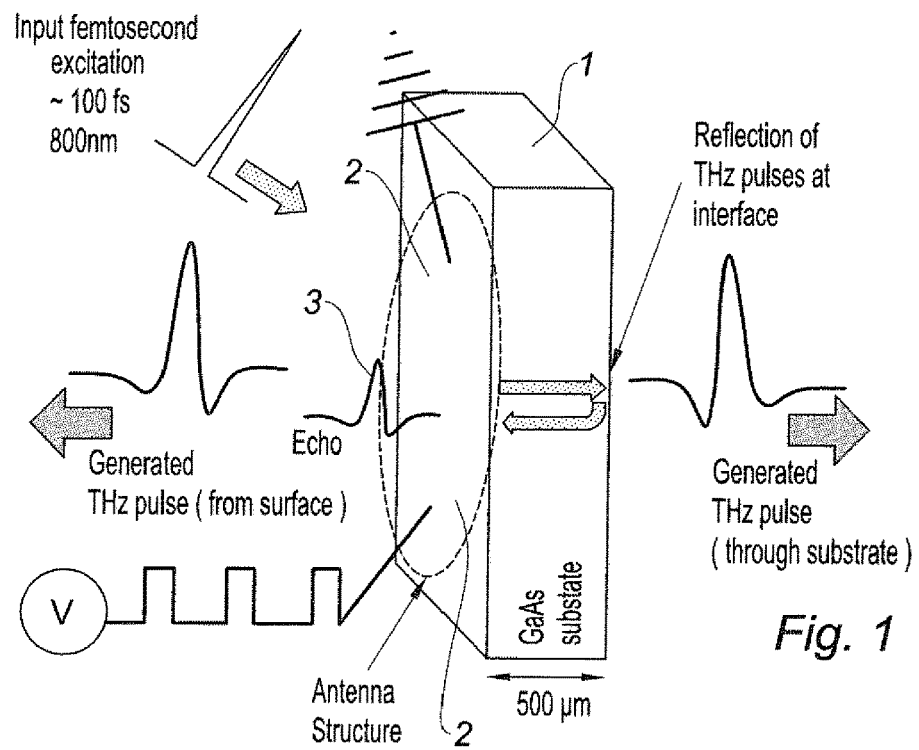
*Fig. 1*
*Prior Art*
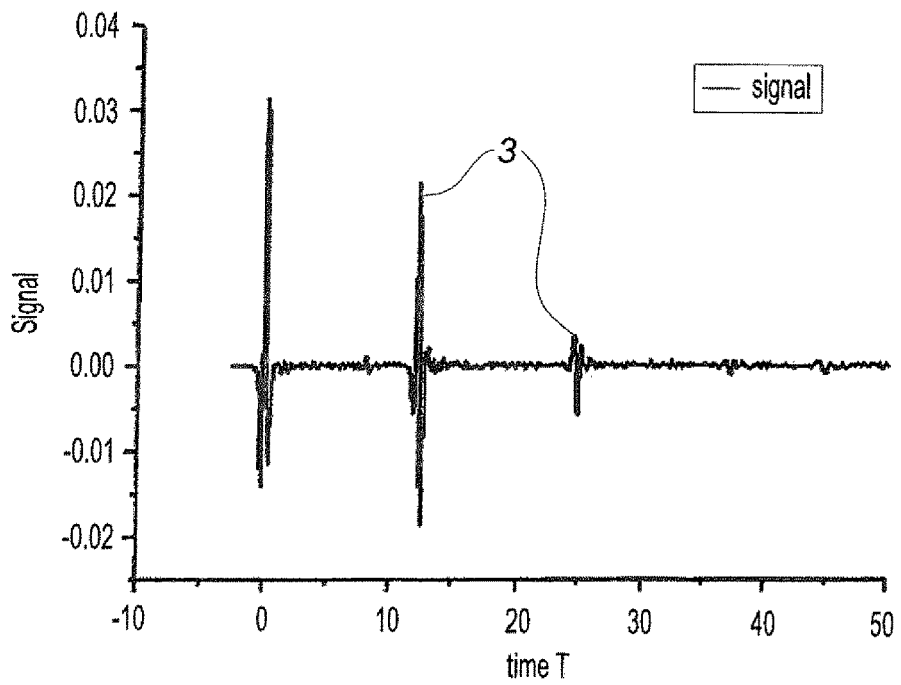
*Prior Art*  *Fig. 2*

PHOTOCONDUCTIVE ANTENNA FOR TERAHERTZ WAVES, METHOD FOR PRODUCING SUCH PHOTOCONDUCTIVE ANTENNA AND TERAHERTZ TIME DOMAIN SPECTROSCOPY SYSTEM

TECHNICAL FIELD

The present invention relates generally to a photoconductive antenna, a method for producing a photoconductive antenna and a terahertz time domain spectroscopy.

BACKGROUND ART

The terahertz (THz) frequency range, which lies between the microwave and mid-infrared ranges, offers unique opportunities in a variety of application domains which include medical and security imaging, non-destructive testing, submillimetre-astronomy and the detection of gases.

Over the last decade, technological solutions have emerged that are extremely promising to cover the lack of devices in this part of the electromagnetic spectrum. One of the most important and widespread technique is THz time domain spectroscopy called TDS. It is based around optical ultrafast lasers for the generation and detection of THz pulses. The generation of THz pulses is usually performed through ultrafast excitation of photoconductive antennas.

Referring to FIG. 1, a photoconductive antenna has usually a particular substrate (1), usually a semiconductor, with two electrodes (2) on the substrate (1). The mechanism is as follows: irradiating the gap between the electrodes (2) with ultrashort pulse laser light while applying a voltage across the electrodes (2) causes excited photocarriers to induce an instantaneous current flow between the electrodes (2), and the photoconductive antenna emits a terahertz wave with a broad frequency spectrum. It should be noted that THz-TDS systems can use another photoconductive antenna or an electro-optic crystal as a detector for terahertz waves.

In a typical semiconductor antenna, the particular semiconductor can be selected from compound semiconductors such as GaAs, InGaAs, AlGaAs, GaAsP, and InGaAsP. Further, low-temperature-grown GaAs (LT-GaAs) films, grown in the crystalline form are very commonly used (IEEE J Quant. Elect. 28 2464 (1992)) for short carrier lifetime and large resistance. LT-GaAs is grown as a crystal on a semi-insulating GaAs (SI—GaAs) substrate in most cases. This causes various problems while THz waves pass through the SI-GaAs substrate, such as reduced efficiency of use of the power of the THz waves and spectral narrowing.

To overcome the drawback of spectral narrowing, a multilayered antenna has been developed. This is disclosed in US patent application US 2014/0252379, which discloses a photoconductive antenna that generates and detects terahertz waves, and has a substrate without refractive index dispersion, a buffer layer, a first semiconductor layer, a second semiconductor layer, and an electrode in this order. The substrate is made of Si, the buffer layer contains Ge, and the first and second semiconductor layer both contain Ga and As. The element ratio Ga/As of the second semiconductor layer is smaller than the element ratio Ga/As of the first semiconductor layer.

THz-TDS characteristics, including the dynamic range, bandwidth, signal-to-noise ratio and frequency resolution are closely related to the pulse specifications; consequently its performances are mainly linked to the characteristics of the pulse emitter.

More specifically, a THz-TDS has a frequency resolution limited by the total scanning time, which is mainly limited by unwanted interfering echoes (3) of the emitted THz pulse—see FIG. 2. Indeed, the problem of having echoes arises when the original signal is reflected from discontinuities, such as change in refractive index, on the beam path.

If most of the echoes are manageable (for instance by means of samples, windows electro-optic detection crystals with thicker or wedged dimensions), in the case of photoconductive antenna, an echo arises from the reflection of the original pulse in its own substrate. Because of the short distances of a standard size wafer, it is this echo that limits in practice the spectral resolution of the system. With a photoconductive antenna made out of a 500 µm GaAs wafer (n=3.64 refractive index in the THz range), a THz echo arises after only 12 ps, limiting the resolution to a lower bound of typically 90 GHz (3 $cm^{-1}$).

Although such a resolution is low enough for many applications, several applications require better performances. For example, spectroscopic methods for the sensing and identification of gases have shown great promise, owing to their inherent non-invasive nature, but also because they are highly selective. Compared to mid-IR spectrum, which consists of complex signature of vibrational and rovibrational transitions, the THz fingerprint of many polar molecules consist of simple rotational spectra with unique spectral signature, which may provide more efficient and accurate detection of many gases. To resolve such spectrums, higher resolution is needed, since most of pure rotational spectrum spacing typically ranges from 0.1 $cm^{-1}$ to 10 $cm^{-1}$ (e.g. rotational constant B=2 $cm^{-1}$ for CO molecule).

For higher spectral resolution in THz-TDS systems, several methods have been proposed to deal with echoes issue. THz anti-reflection coatings have been developed but have several drawbacks: the dielectric ones are wavelength dependent (IEEE Microwave and guided wave letters, Col. 10, No. 7, Jul. 2000 "An anti-Reflection coating for silicon optics at terahertz frequencies" A. J. Gatesman, J. Waldman, M. Ji, C. Musante, and S. Yngvesson), while broadband design might be achieved with thin metal coating (Physical Review B 77, 195405; 2008; "Nanostructured gold films as broadband terahertz antireflection coatings"; Andreas Thoman, Andreas Kern, Hanspeter Helm, and Markus Walther)[1] but are difficult to realize and introduce important losses.

Alternative approaches apply numerical methods, either by deconvolution with reference signal, or echo cancelation with a deconvolution algorithm.

However, these methods require either a careful calibration through a reference in the first case, or an assumption of the dispersion properties of the substrate in the later. As a consequence, due to complexity of the acquired THz signals, it can add artefacts in calculated spectrum.

Finally, the last method consists simply in processing antennas on a thicker substrate so as to displace the echoes to later times, but does not eliminate them. Moreover, emitted power is distributed between echoes and the main pulse, which in a sense constitutes a power loss.

To overcome the above-mentioned limitations, a need exists for a novel antenna design that intrinsically suppresses echoes that usually originate from antenna's substrate reflection, without any numerical post-processing, and which is not affected by losses.

SUMMARY OF THE INVENTION

It is therefore an object of the invention to provide a photoconductive antenna that generates and/or detects terahertz waves, the photoconductive antenna comprising at least one substrate and at least one electrode onto the front face of the substrate, characterized in that it comprises at least one layer obtained in a material reflective to terahertz waves, said layer extending below the front face of the substrate at a distance lower than the wavelength.

Said layer extends at a distance comprised between 5 and 10 μm below the front face of the substrate.

Moreover, the layer is preferably a metal layer.

Said metal is chosen among the following list of gold and/or titanium and/or silver and/or copper.

Furthermore, the substrate is a semiconductor substrate chosen among the following list of GaAs, InGaAs, AlGaAs, GaAsP, Si, quartz and InGaAsP.

Another object of the invention concerns a method for producing a photoconductive antenna that generates and/or detects terahertz waves, the method comprising at least the following steps of:

forming a layer on a first substrate, said layer forming a selective etch stop;
forming a layer on the selective etch stop layer ;
forming a layer obtained in a material reflective to terahertz waves on the layer;
bonding a second substrate onto the layer obtained in a material reflective to terahertz waves;
removing the layer and the first substrate;
forming at least one electrode onto the layer.

The layer obtained in a material reflective to terahertz waves is formed onto the GaAs layer by metal evaporation.

The metal is preferably chosen among the following list of gold and/or titanium and/or silver and/or copper.

Furthermore, the first and second substrates are obtained from compound semiconductors chosen among the following list of GaAs, InGaAs, AlGaAs, GaAsP, Si, quartz and InGaAsP Moreover, the selective etch layer and the first substrate are removed using mechanical and/or chemical etching method and the electrode is formed by photolithography and/or electron-beam lithography.

A last object of the invention concerns a terahertz time domain spectroscopy system comprising a generator section that generates a terahertz wave and a detector section that detects the terahertz wave, at least one of the generator section and the detector section comprising the photoconductive antenna according to the invention.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the drawings:

FIG. 1 is a schematic view of a prior art photoconductive antenna,

FIG. 2 shows a time domain terahertz pulse generated by a prior art photoconductive antenna.

DETAILED DESCRIPTION OF THE INVENTION

Figure 3:
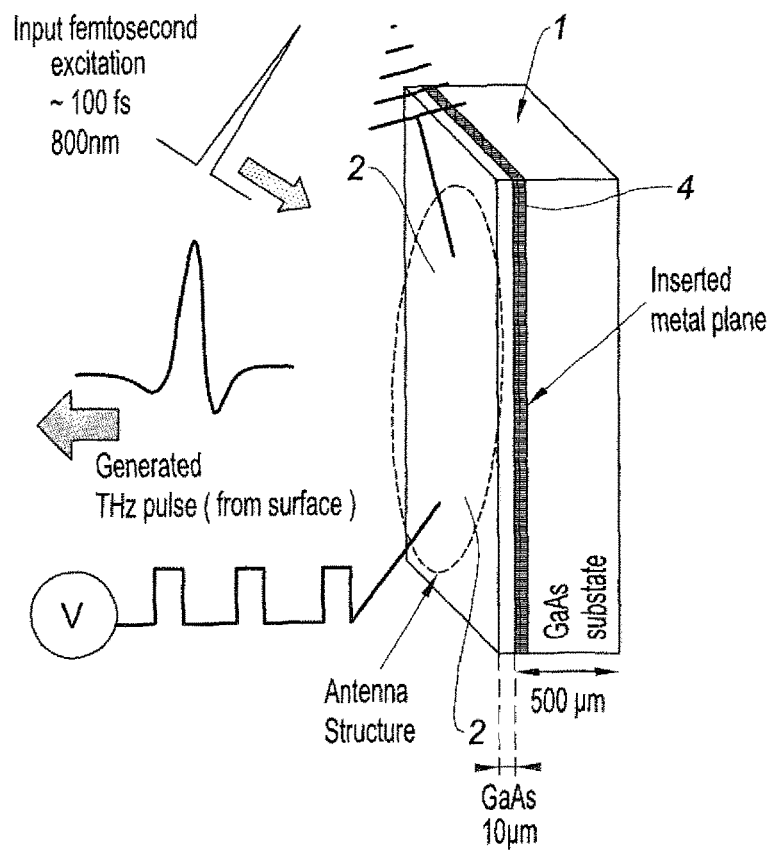
FIG. 3 is a schematic view of a photoconductive antenna according to the present invention.

Referring to FIG. 3, the photoconductive antenna that generates and/or detects terahertz waves comprises a substrate (1) and two electrodes (2) onto the front face of the substrate (1). The photoconductive antenna further comprises a layer (4) obtained in a material reflective to terahertz waves, said layer extending below the front face of the substrate (1) at a distance shorter than the wavelength. Said layer (4) is preferably a metal layer and extends at a distance comprised between 5 and 10 μm below the front face of the substrate (1) compared to a wavelength greater than 20 μm of the THz wave within the material. The substrate (1) is a semiconductor which can be selected from compound semiconductors such as GaAs, InGaAs, AlGaAs, GaAsP, Si, quartz and InGaAsP. Preferably, the substrate (1) is a non doped GaAs substrate, since non doped substrate allows the metal reflective layer (4) to be floating and not connected to the ground, and said metal of the layer (4) is chosen among the following list of gold and/or titanium and/or silver and/or copper.

Figure 4:
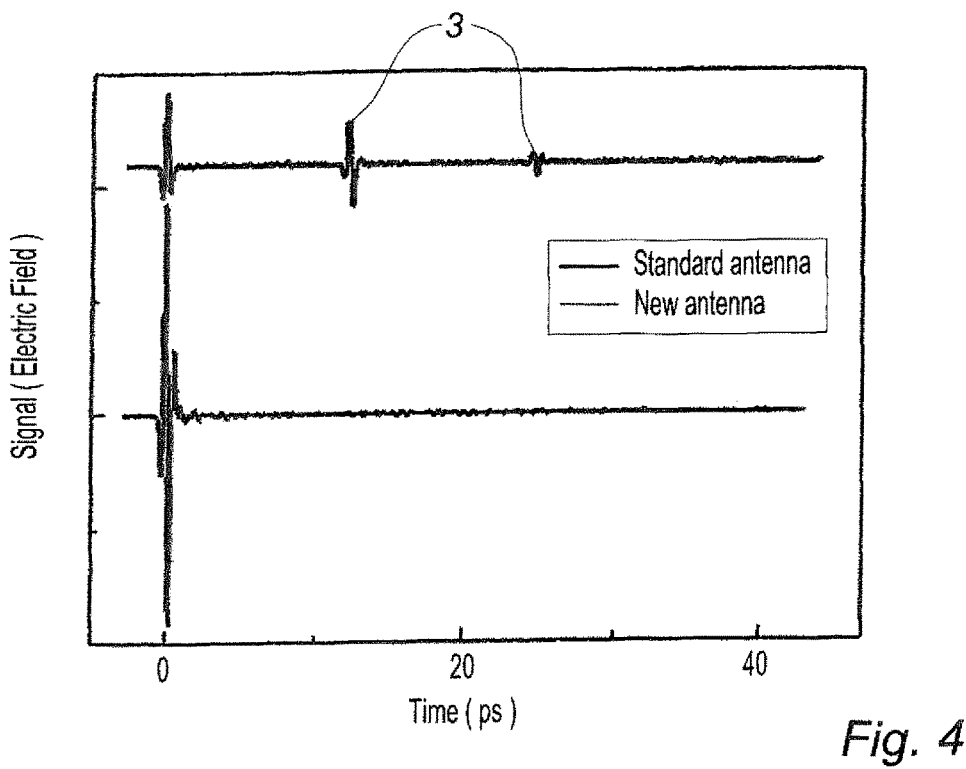
FIG. 4 shows a time domain terahertz pulse generated by a photoconductive antenna according to the invention compared to a time domain terahertz pulse generated by a prior art photoconductive antenna.

As there is no possibility of the THz pulse to propagate beyond the inserted metal plane, referring to FIG. 4, this eliminates the echo that results from the interface between the substrate and air. Further, as there are no echoes from this system, all the THz power is in the original THz pulse resulting in a higher extraction of power generated. FIG. 4 shows the typical time scans of the emitted THz field that can be obtained for a standard THz antenna and the new echo-less THz antenna. In the case of the standard antenna (with typical 500 μm thick Ga As substrate), the main THz emission is seen at 0 ps followed by a series of echoes (3) at multiples of 12 ps that arise from the reflections of the original THz pulse within its substrate. For the antenna according to the invention, the main THz pulse can be observed at 0 ps but no echoes are observed. Since no THz emission is permitted to generate echoes, all the THz power is extracted from the surface, thus the output field is increased.

Figure 5:
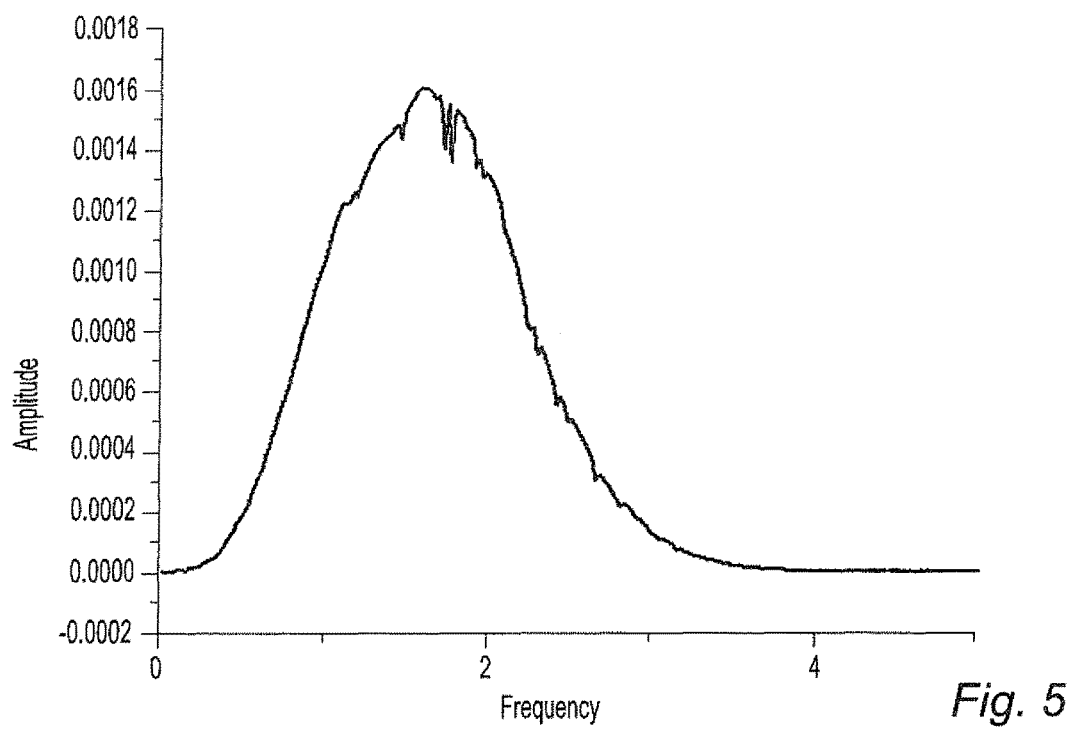
FIG. 5 shows the spectral response of the terahertz pulse generated by a photoconductive antenna according to the invention.
Figure 6:
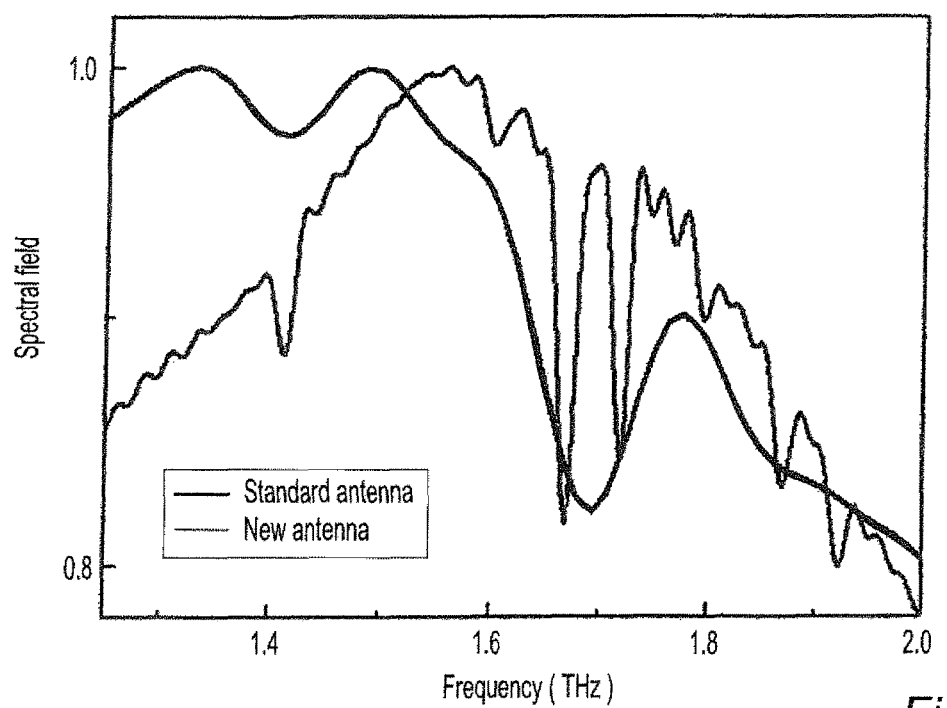
FIG. 6 shows a zoom of the spectral field of a time domain terahertz pulse generated by a photoconductive antenna according to the invention, showing an increase in resolution when compared to an antenna of the prior art.

Referring to FIGS. 5 and 6 which shows the spectrum obtained from the above time scans (Fourier transform of time scans) in the spectral range of 1.25 THz to 2.0 THz, we can observe that the absorption peak is not resolved in the case of the prior art antenna (FIG. 6) while the peaks are clearly resolved with a double peak structure observed around 1.7 THz in the case of the antenna according to the invention (FIGS. 5 and 6) whilst a single peak was observed for the prior art antenna.

Figure 7A:
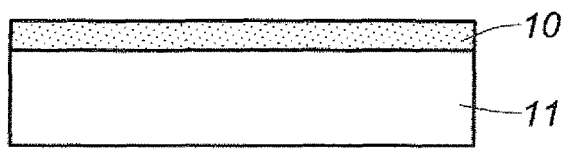
FIG. 7A to 7G are schematic views of the different steps of the method for producing a photoconductive antenna according to the invention.
Figure 7B:
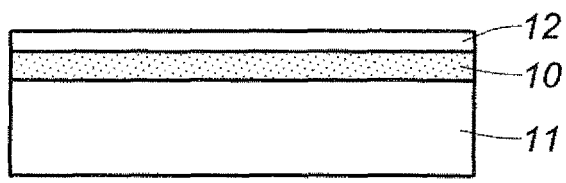
Figure 7C:
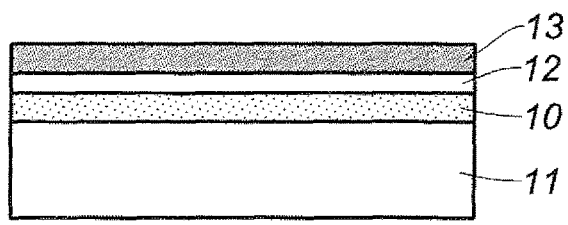
Figure 7D:
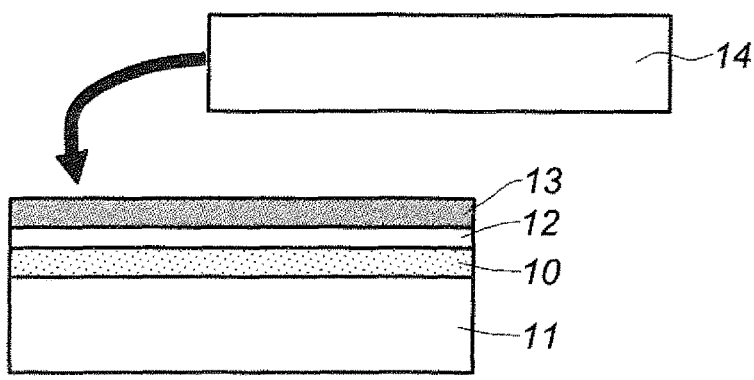
Figure 7E:
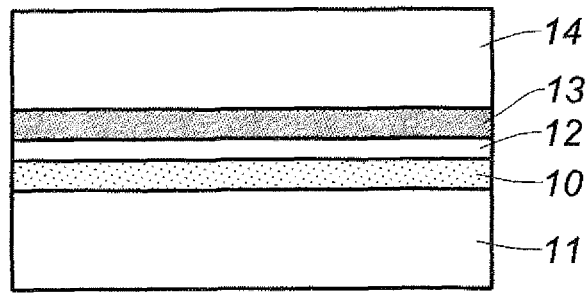
Figure 7F:
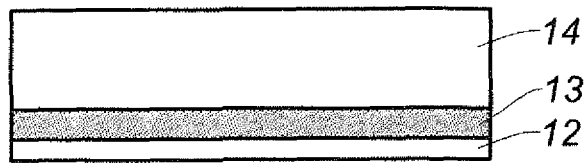
Figure 7G:
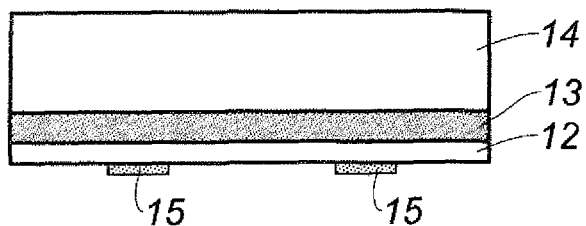

FIGS. 7A to 7G shows the different steps for producing a photoconductive antenna that generates and/or detects a terahertz wave according to the invention. The method comprises at least the following steps of forming a AlGaAs layer (10) on a first GaAs substrate (11) (FIG. 7A), said AlGaAs layer (10) forming a selective etch stop, forming a GaAs layer (12) on the selective etch stop AlGaAs layer (10) (FIG. 7B), forming a layer (13) obtained in a material reflective to terahertz waves on the GaAs layer (12) (FIG. 7C), using metal evaporation, for example, and bonding a second substrate (14) onto the layer (13) obtained in a material reflective to terahertz waves (FIGS. 7D and 7E). Said second substrate (14) is usually also coated with the same metal layer as the first GaAs substrate (11). Then, referring to FIG. 7F, the AlGaAs layer (10) and the first GaAs substrate (11) are removed by any appropriate method, such as mechanical and/or chemical etching method, and at least one electrode (15) is formed onto the GaAs layer (12) (FIG. 7G) by photolithography and/or electron-beam lithography.

The material reflective to terahertz waves can be formed on the GaAs layer using any appropriate method well known by the man skilled in the art without departing from the scope of the invention. Moreover, the metal is preferably chosen from the following list of gold and/or titanium and/or silver and/or copper but the metal can be substituted by any material reflective to terahertz waves.

Figure 8:
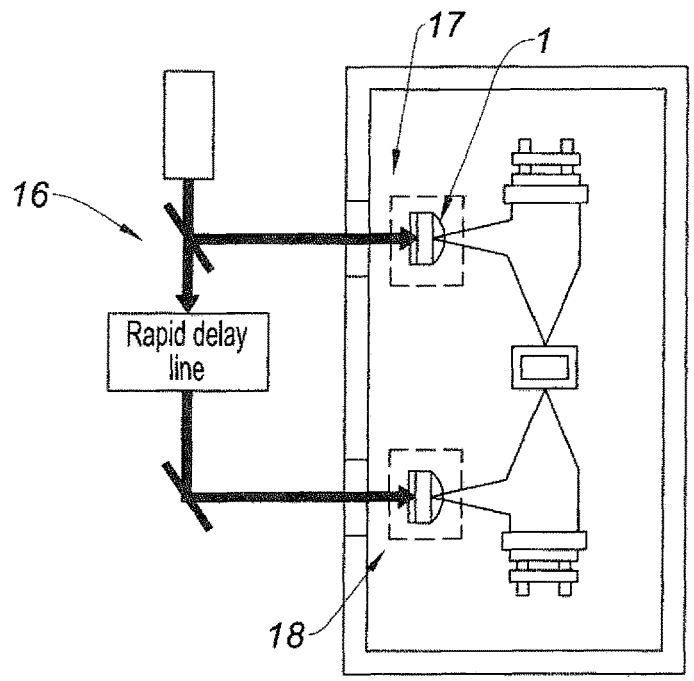
FIG. 8 is a schematic representation of a terahertz time domain spectroscopy system comprising at least one photoconductive antenna according to the invention.

Referring to FIG. 8, the photoconductive antenna according to the invention is intended to be used in a terahertz time domain spectroscopy system 16 comprising at least a generator section 17 that generates a terahertz wave and a detector section 18 that detects the terahertz wave, at least one of the generator section 17 and the detector section 18 having the photoconductive antenna according to the invention. In this embodiment, the generator section 17 has the photoconductive antenna according to the invention.

It should be noted that the photoconductive antenna according to the invention can also be used for continuous wave THz systems, such as continuous wave THz spectrometer, without departing from the scope of the invention.

EXAMPLE

Figure 9:
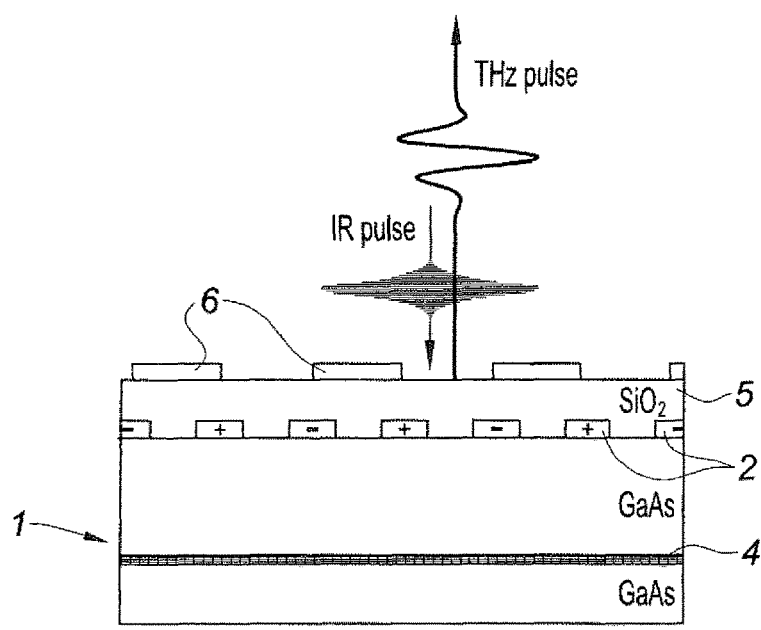
FIG. 9 is a schematic sectional view of one embodiment of a photoconductive antenna according to the invention.

Referring to FIG. 9, a metal-metal interdigitated photoconductive antenna is disclosed.

A photoconductive antenna is based on the ultra-fast acceleration and deceleration of optically generated carriers under an applied bias field across the antenna gap. This generates a time-varying electrical current and consequently a radiated electrical field proportional to its temporal derivative. Time profile of this current is both related to the optical excitation pulse length and the carrier recombination time in the substrate. A variant of the photoconductive antenna is based on an interdigitated geometry known to be an efficient way to generate THz pulses. In addition, it delivers a strong emitted field with good directivity since a large area is illuminated (~500 μm diameter), and a low bias is needed owing to the possibility of a small electrode spacing.

So-called interdigitated photoconductive (IPC) antennas are processed as follows. A first metallization layer of 5 nm Cr and 150 nm Au for the interdigitated electrodes (2) is made on an undoped GaAs wafer, using a lift-off technique with AZ5214 negative photoresist and UV photolithography. Electrodes (2) are 4 μm wide, equally spaced by a distance Δ. A 500 nm-thick layer of $SiO_2$ (5) is deposited over the first metallization layer. The second metallic layer is composed of metallic fingers (6) covering gaps with a periodicity double that of the first. This permits optical excitation of every second period of the gaps of the first metallization and hence excitation of only one bias field direction, avoiding destructive interferences of the generated THz far field. Electrodes (2) polarize the GaAs substrate (1) with an electric field of typically 10 kV/cm. A femtosecond IR pulse photo-excites carriers in the substrates, which are then accelerated by the electrical field generated by the electrodes (2). For standard IPC antenna, THz radiation is emitted both in air and in the GaAs substrate, resulting in an unwanted echo after reflection. To prevent this, a gold plane (4) is inserted at a distance d from the interdigitated electrodes (2). The distance d is chosen such that the GaAs layer is smaller than emitted wavelength, so it can be considered infinitely thin on the wavelength scale, and suppress therefore the formation of any echo. It can be also viewed in a time-domain approach: the thickness of substrate is chosen to be so small that all echoes are emitted on a time scale smaller than the mean oscillation period of the radiation. For standard IPC antennas, the spectrum ranges typically from 100 GHz to 4 THz, corresponding to wavelengths ranging from 75 μm to 3 mm in air and from 22 μm to 900 μm in GaAs. Therefore, a d=10 μm length corresponds to the wave propagation limit ($\lambda/2$ criterium) in GaAs for a radiation below 4 THz.

Such a so-called metal-metal (MM) IPC was processed as follow. The 10 μm thick undoped GaAs layer was grown using molecular beam epitaxy (MBE). The growth was performed on a GaAs substrate on which an AlGaAs selective etch stop layer was grown, followed by the 10 μm thick undoped GaAs layer. Then, a metal layer (Ti/Au) was evaporated on top of the grown layers, which corresponds to the gold plane. After a standard wafer bonding technique on semi-insulating GaAs substrate, the original wafer and the AlGaAs layer were removed through mechanical and chemical methods, leaving the 10 μm GaAs layer on top of the echo-suppressing metal layer. Then, standard IPC process is realized on this layer.

Such an antenna has been used in a TDS system to evaluate its performances compared with a standard IPC one, grown on a 500 μm thick undoped GaAs wafer. Since the gold plane prevents any THz transmission in substrate, both antennas are used in reflection. A Ti:Sapphire femtosecond laser, with pulse duration of typically 100 fs and a repetition rate of 77 MHz, is used both to generate the THz pulse and to detect the THz emitted. About 130 mW average power is focused on the MM-IPC antenna, polarized with a 4V voltage. THz is collected with a parabolic mirror (3" diameter) and coupled to a TDS system. The THz-TDS setup is inserted in a low-humidity chamber (typically 2% humidity) to prevent absorption of THz radiation from water. The THz beam and the femtosecond beam are focused onto a 200 μm thick (110) ZnTe crystal with parabolic mirrors for electro-optic sampling (EOS). As a comparison, the THz signal emitted by standard IPC with 500 μm thick GaAs substrate has been measured in the same experimental conditions, and the same electrical bias field (10 kV/cm).

Since the THz pulse is not partially back-reflected in the antenna substrate, all the energy is concentrated in the first and only pulse. This provides more intense pulses, with peak amplitude 3 times larger than ones produced with standard IPC antennas and peak-peak amplitude 4 times larger.

According to a particular embodiment of the invention, the metal-metal interdigitated photoconductive antenna of FIG. 9 presents, in addition to the constraints on thickness of the GaAs, or any other cited material, layer, $d=\lambda/2$ where $\lambda$ corresponds to the maximum frequency that needs to be emitted/detected, the geometry of the surface contacts is also critical to the operation of the device. In an interdigitated geometry the separation of the contacts Δ need to be at most d/2. This permits the field across the contacts to be greater than between the antenna structure and the buried metal plan. This allows the echo to be suppressed without effecting considerably the spectral response of the device.

The use of the interdigitated geometry also permits the applications of Si lenses to be avoided.

The advantage here comes from the use of this interdigitated geometry combined with the buried metal layer to suppress the echoes from standard THz systems.

In a particular embodiment of the invention, the metal-metal interdigitated photoconductive antenna of FIG. 9 is used for detection. When the antenna of FIG. 9 is used in detection, an echo was still present from the detection device. It is possible to remove all the echoes from the THz system by replacing the GaAs layer with the thickness d between the electrodes (2) and the layer of the reflective layer (4), with a layer of material having an ultrafast response, such as LT-GaAs, ErAs:GaAs, Fe:InGaAs or InGaAsN. In an embodiment, the GaAs layer has been separated in to three layers. The top layer is 2 µm thick LT-GaAs, below which is a 300 nm AlGaAs (with 30% Al) as an electron blocking layer, followed by 3.7 µm thick GaAs layer. This gives a total thickness of d=6 µm. The distance Δ also needs to be adjusted to less than 3 µm as highlighted above for the source. This antenna designed for detection may also be used as a source. It is to be noted here that the so-called GaAs layer may be constituted of any cited material such as GaAs, InGaAs, AlGaAs, GaAsP, Si, quartz, InGaAsP, LT-GaAs, ErAs:GaAs, Fe:InGaAs or InGaAsN for example, both in emission and in detection.

Although embodiments of the present disclosure have been described in detail, those skilled in the art should understand that they may make various changes, substitutions and alterations herein without departing from the spirit and scope of the present disclosure. Accordingly, all such changes, substitutions and alterations are intended to be included within the scope of the present disclosure as defined in the following claims.

For example, photoconductive antennas according to the invention may have an additional layer of SiO2 in front of the substrate and the electrodes and a second metallic layer composed of metallic fingers covering gaps.

In the claims, means-plus-function clauses are intended to cover the structures described herein as performing the recited function and not only structural equivalents, but also equivalent structures.

The invention claimed is:

1. A metal-metal interdigitated photoconductive antenna that generates and/or detects terahertz waves, the photoconductive antenna comprising at least one substrate (1) and interdigitated electrodes (2) on a face, called the front face, of the at least one substrate (1), characterized in that:
   it comprises at least one layer (4) formed of a material reflective to terahertz waves, said at least one layer (4) located inside the at least one substrate (1) at a distance from the front face of the at least one substrate lower than the wavelength of said terahertz waves; and
   it comprises an interdigitated geometry on said front face of the at least one substrate (1) comprising:
   a first metallic layer of 5 nm Cr and 150 nm Au for the interdigitated electrodes (2), equally spaced by a distance Δ, is made on said front face of the at least one substrate (1);
   a 500 nm-thick layer of SiO2 (5) deposited over the first metallic layer; and
   a second metallic layer composed of metallic fingers (6) covering gaps between said interdigitated electrodes with a periodicity double that of the distance Δ.

2. The metal-metal interdigitated photoconductive antenna according to claim 1 characterized in that the at least one layer (4) extends at a distance comprised between 5 and 10 µm below the front face of the at least one substrate (1).

3. The metal-metal interdigitated photoconductive antenna according to claim 1, characterized in that the at least one layer (4) is a metal layer.

4. The metal-metal interdigitated photoconductive antenna according to claim 3 characterized in that the metal is chosen among the following list of gold and/or titanium and/or silver and/or copper.

5. The metal-metal interdigitated photoconductive antenna according to claim 1, characterized in that the at least one substrate (1) is a semiconductor substrate chosen among the following list of GaAs, InGaAs, AlGaAs, GaAsP, Si, quartz, InGaAsP, LT-GaAs, ErAs:GaAs, Fe:InGaAs or InGaAsN.

6. The metal-metal interdigitated photoconductive antenna according to claim 1 characterized in that the thickness of the substrate layer between said interdigitated electrodes (2) and said at least one layer (4) is d=λ/2 where λ corresponds to the maximum frequency that needs to be emitted/detected.

7. The metal-metal interdigitated photoconductive antenna according to claim 6, characterized in that the distance Δ between interdigitated electrodes (2) is at most d/2.

8. The metal-metal interdigitated photoconductive antenna according to claim 1, characterized in that the substrate layer between said interdigitated electrodes (2) and said at least one layer (4) is made of a material with LT-GaAs, ErAs:GaAs, Fe:InGaAs or InGaAsN.

9. The metal-metal interdigitated photoconductive antenna according to claim 8, characterized in that the substrate layer between said interdigitated electrodes (2) and said at least one layer (4) is made of three layers, the top layer is 2 µm thick and made of LT-GaAs, ErAs:GaAs, Fe:InGaAs or InGaAsN, below which is a 300 nm AlGaAs followed by 3.7 µm thick GaAs layer; the distance Δ between interdigitated electrodes (2) being less than 3 µm.

10. A method for producing a metal-metal interdigitated photoconductive antenna according to claim 1, the method comprising at least the following steps of:
   Forming a first layer (10) on a first substrate (11), said first layer (10) forming a selective etch stop;
   Forming a second layer (12) on the selective etch stop first layer (10);
   Forming a third layer (13) in a material reflective to terahertz waves on the second layer (12);
   Bonding a second substrate (14) onto the third layer (13) obtained in a material reflective to terahertz waves;
   Removing the selective etch layer (10) and the first substrate (11);
   Forming interdigitated electrodes (15) onto the second layer (12).

11. The method for producing a photoconductive antenna according to claim 10 characterized in that the third layer (13) obtained in a material reflective to terahertz waves is formed onto the second layer (12) using metal evaporation.

12. The method for producing a photoconductive antenna according to claim 10, characterized in that the third layer is made of metal chosen among the following list of gold and/or titanium and/or silver and/or copper.

13. The method for producing a photoconductive antenna according to claim 10, characterized in that the first substrate (11) and second substrate (14) are obtained from compound semiconductors chosen among the following list of GaAs, InGaAs, AlGaAs, GaAsP, Si, quartz and InGaAsP.

14. The method for producing a photoconductive antenna according to claim 10, characterized in that the first layer (10) and the first substrate (11) are removed using mechanical and/or chemical etching method.

15. The method for producing a photoconductive antenna according to claim 10, characterized in that the interdigitated electrodes (15) are formed by photolithography and/or electron-beam lithography.

16. A terahertz time domain spectroscopy system (16) comprising a generator section (17) that generates a terahertz wave and a detector section (18) that detects the terahertz wave, at least one of the generator section (17) and the detector section (18) comprising the metal-metal interdigitated photoconductive antenna according to claim 1.

* * * * *